United States Patent [19]

Connor et al.

[11] 4,117,134
[45] Sep. 26, 1978

[54] 4,5-DIHYDRO-4,5-DIOXO-1H-1-BENZOPYRANO (2,3-B)-PYRIDINE-3-CARBOXYLIC ACIDS, SALTS AND ESTERS

[75] Inventors: David T. Connor, Ann Arbor, Mich.; Maximilian von Strandtmann, New Castle, Del.

[73] Assignee: Warner-Lambert Company, Morris Plains, N.J.

[21] Appl. No.: 806,026

[22] Filed: Jun. 13, 1978

[51] Int. Cl.² .................. C07D 405/04; A61K 31/535
[52] U.S. Cl. .............................. 424/256; 260/295.5 T
[58] Field of Search ................... 260/295.5 T; 424/256

[56] References Cited
FOREIGN PATENT DOCUMENTS 2,416,519 10/1975 Fed. Rep. of Germany .... 260/295.5 T
47-20,627 6/1972 Japan ................................. 260/295.5 T Primary Examiner—John M. Ford
Attorney, Agent, or Firm—Albert H. Graddis; Frank S. Chow; Anne M. Kelly

[57] ABSTRACT

This invention relates to compounds of the formula

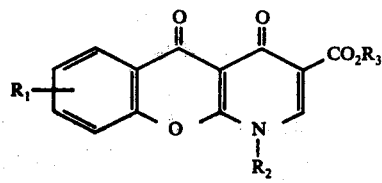

wherein $R_1$ is hydrogen, lower alkyl, halogen, hydroxy or lower alkoxy; $R_2$ is hydrogen or lower alkyl; $R_3$ is hydrogen or lower alkyl; and the pharmaceutically acceptable, non-toxic salts thereof. The compounds of the invention are active in the prevention of allergic and asthmatic reactions in mammals.

8 Claims, No Drawings

4,5-DIHYDRO-4,5-DIOXO-1H-1-BENZOPYRANO (2,3-B)-PYRIDINE-3-CARBOXYLIC ACIDS, SALTS AND ESTERS

BACKGROUND OF THE INVENTION

1. Field of the invention

This invention relates to 4,5-dihydro-4,5-dioxo-1H-1-benzopyrano[2,3-b]pyridine-3-carboxylic acids, their esters and the non-toxic pharmaceutically acceptable salts thereof, which are active in the prevention of allergic and asthmatic reactions in mammals.

2. Description of the Prior Art

United States application Ser. No. 736,788, filed Oct. 29, 1976 now U.S. Pat. No. 4,046,769 and United States application Ser. No. 736,926, filed Oct. 29, 1976, now U.S. Pat. No. 4,066,655 disclose structurally distinct benzopyrancarboxylic acids which also demonstrate anti-allergic and anti-asthmatic activity. Specifically, United States application Ser. No. 736,788 describes 4,10-dihydro-4,10-dioxo-1H-1-benzopyrano (3,2-b) pyridine-2-carboxylic acids; and United States application Ser. No. 736,926 describes 4,10-dihydro-4,10-dioxo-1H-1-benzopyrano(3,2-b)pyridine-3-carboxylic acids.

DESCRIPTION OF THE PARTICULAR EMBODIMENTS

This invention relates to compounds of the formula:

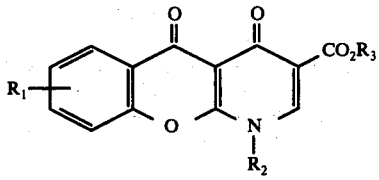

wherein $R_1$ is hydrogen, lower alkyl, halogen, hydroxy or lower alkoxy; $R_2$ is hydrogen or lower alkyl; $R_3$ is hydrogen or lower alkyl.

Also embraced within the scope of this invention are the non-toxic, pharmaceutically acceptable salts of compounds of the formula VII, for example, the calcium salt, the sodium salt and the like.

Componds of the formula VII are prepared in accordance with the following reaction scheme:

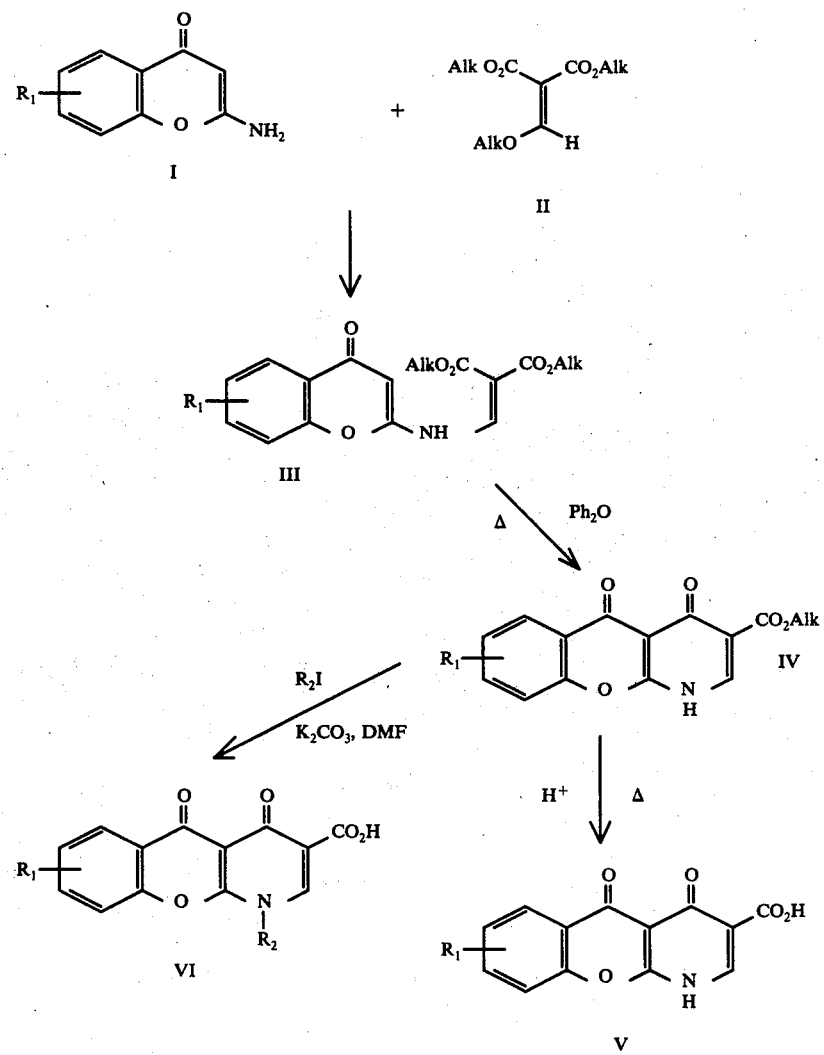

Referring to the above reaction scheme, the substituted 2-aminochromone starting material I is reacted with a dialkyl alkoxymethylenemalonate II, typically at a temperature of about 130° C. until a homogenous solution is formed. The dialkyl{[(4-oxo-4H-substituted-1benzopyran-2-yl)amino]methylene}-malonate III obtained is refluxed under nitrogen in diphenyl ether for at least 90 minutes to achieve cyclization and obtain the alkyl 4,5-dihydro-4,5-dioxo-substituted-1H-1-benzopyrano[2,3-b]-pyridine-3-carboxylate IV. The product IV is then hydrolyzed to obtain the 3-substituted carboxylic acid product V, or alkylated on the ring nitrogen to obtain the final product of the formula VI. In aforementioned formulas I, II, III, IV, V and VI, $R_1$ is hydrogen, lower alkyl, halogen, hydroxy or lower alkoxy; $R_2$ is hydrogen or lower alkyl; and Alk is lower alkyl.

The starting 2-aminochromone I, is prepared by reacting an appropriately substituted methyl salicylate with a sodio compound which is prepared by reacting a solution of acetonitrile in anhydrous ether with a solution of sodium amide in liquid ammonia, according to the method of Y. Kawase and K. Sakashita, Bulletin Chem. Soc. Japan, 35 (11) 1869 (1962). The disclosure in this reference is incorporated herein.

The compounds of this invention are active in the prevention of allergic conditions (typically, asthmatic reactions) in mammals such as rats as evidenced by positive results in the passive cutaneous anaphylaxis screen (PCA test). The PCA screen is a modification of the procedure described by I. Mota, *Life Sciences*, Vol. 4, No. 7: 465–474 (1963) and Z. Ovary and O. Bier, Proc. *Soc. Exptl. Biol. Med.*, 81: 584–586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angioneurotic edema, atopic dermatitis, including infantile eczema, urticaria, dermographism, dermatoconjunctivitis, acute allergic conjunctivitis, chronic allergic conjunctivitis, and the like.

Inhibition of reaginic antigen/antibody reactions in experimental animals such as rats is regarded as respresentative of inhibition of human reaginic antigen-/antibody reactions which occur during allergic episodes.

Thus, the compounds of this invention having the formula VII are active for the inhibition of reagin-mediated allergic disorders in mammals in need thereof at dose levels of from about 0.5 to about 100 mg/kg of body weight when administered parenterally or by pulmonary administration via the buccal cavity. Thus, for example, 4,5-dihydro-4,5-dioxo-1H-1-benzopyrano[2,3-b]pyridine-3-carboxylic acid (the compound of Example 3 ) shows a 100% inhibition of the allergic response at 0.5 mg/kg when administered intervenously to rats in the passive cutaneous anaphalaxis (PCA) screen. Accordingly, the compounds of this invention having the formula VII are useful in the treatment of asthma, hay fever and other allergic conditions.

In use, the compounds of the invention having the furmula VII may be combined with parenterally acceptable vehicles, such as gum tragacanth, in saline suspension, to provide dosage forms suitable for parenteral administration.

For pulmonary administration, the compounds of the invention having the formula VII in dry powder form may be formulated with non-toxic, pharmaceutically acceptable propellants known to the pharmacist's art or they may be dispensed in powder form from a powder inhalation device. Compositions in the form of dry powders preferably may include a solid fine powder diluent.

In all of the above formulas I through VII, the R group definitions may be more fully described as follows: the term "lower alkyl" is meant to include lower aliphatic hydrocarbons having 1 to 7 carbon atoms (preferably 1 to 4 carbon atoms) in the carbon chain, such as methyl, ethyl, propyl, isopyropyl, butyl or isobutyl. This definition for lower alkyl also applies to the lower alkyl portion of "lower akloxy" and to the term "Alk". The term "halogen" is meant to include bromine, chlorine, iodine and fluorine.

To further illustrate the practice of this invention, the following examples are included.

EXAMPLE 1

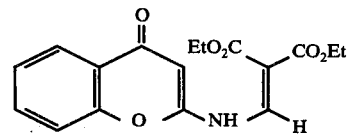

Diethyl{[(4-oxo-4H-1-benzopyran-2-yl)amino]methylene}malonate.

A mixture of 2-aminochromone (3.22 g, 0.02 mole) and diethyl ethoxymethylenemalonate (8.64 g, 0.04 mole) is heated at 130° C. under nitrogen until an homogeneous solution forms (16 hrs.). The reaction mixture is cooled. The product, which precipitated, is filtered off and washed with hexane. Recrystallization from ethylacetate gives pale yellow crystals (6.01 g, 91%), mp 138°–140° C.

Anal. Calcd. for $C_{17}H_{17}NO_6$: C, 61.63; H, 5.17; N, 4.23. Found: C, 61.80; H, 5.17; N, 4.28.

EXAMPLE 2

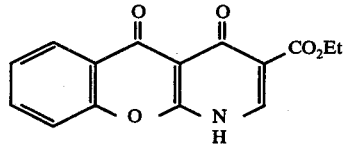

Ethyl 4,5-dihydro-4,5-dioxo-1H-1-benzopyrano[2,3-b]pyridine-3-carboxylate.

Diethyl {[(4-oxo-4H-1-benzopyran-2-yl)amino]methylene}malonate (36 g, 0.11 mole) is added to diphenyl ether (300 ml) at 200° C. The reaction mixture is refluxed under nitrogen for 90 min. The product, which crystallized out on cooling, is filtered off and washed with ethyl acetate. Recrystallization from DMF gives white crystals (25.6 g, 83%), mp 174°–175° C.

Anal. Calcd. for $C_{15}H_{11}NO_5$: C, 63.16; H, 3.89; N, 4.91. Found: C, 63.11; H, 3.87; N, 4.90.

EXAMPLE 3

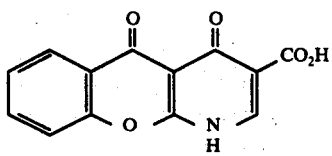

4,5-Dihydro-4,5-dioxo-1H-1-benzopyrano[2,3-b]pyridine-3-carboxylic acid.

A suspension of ethyl 4,5-dihydro-4,5-dioxo-1H-1-benzopyrano[2,3-b]-pyridine-3-carboxylate (3.0 g, 0.011 mole) in 5N hydrochloric acid (100 ml) is refluxed under nitrogen for 16 hrs., cooled, filtered, washed with acetone and sucked dry. Recrystallization from DMF gives white crystals (2.51 g, 93%), mp 335°–340° C.

Anal. Calcd. for $C_{13}H_7NO$: C, 60.71; H, 2.74; N, 5.45. Found: C, 60.51; H, 2.74; N, 5.29.

EXAMPLE 4

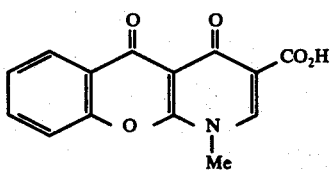

1-Methyl-4,5-dihydro-4,5-dioxo-1H-1-benzopyrano[2,3-b]pyridine-3-carboxylic acid.

A mixture of ethyl 4,5-dihydro-4,5-dioxo-1H-1-benzopyrano[2,3-b]pyridine-3-carboxylate (8 g, 0.028 mole), methyl iodide (17.04 g, 0.12 mole) and potassium carbonate (4.14 g, 0.03 mole) in dimethylformamide (100 ml) is heated at 100° C. for 4 hrs. under nitrogen. The reaction mixture is cooled. The product, which precipitated, is filtered, washed with ethyl acetate and sucked dry. Recrystallization from DMF gives white crystals (3.1 g, 37%), mp 310°–315° C. (dec.).

Anal. Calcd, for $C_{14}H_9NO_5$: C, 61.99; H, 3.34; N, 5.16. Found: C, 61.82; H, 3.45; N, 5.17.

We claim:

1. A compound of the formula VII:

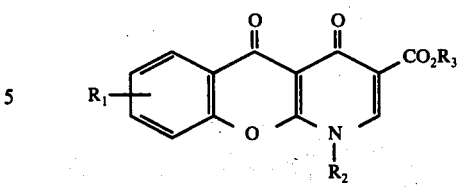

wherein $R_1$ is hydrogen, lower alkyl, halogen, hydroxy or lower alkoxy; $R_2$ is hydrogen or lower alkyl; $R_3$ is hydrogen or lower alkyl; and the pharmaceutically acceptable, non-toxic salts thereof.

2. A compound according to claim 1 wherein $R_1$, $R_2$ and $R_3$ are each hydrogen or lower alkyl.

3. A compound according to claim 1 wherein $R_1$ is hydrogen, and $R_2$ and $R_3$ are each hydrogen or lower alkyl.

4. A compound according to claim 1 which is ethyl 4,5-dihydro-4,5-dioxo-1H-1-benzopyrano[2,3-b]pyridine-3-carboxylate.

5. A compound according to claim 1 which is 4,5-dihydro-4,5-dioxo-1H-1-benzopyran[2,3-b]pyridine-3-carboxylic acid.

6. A compound according to claim 1 which is 1-methyl-4,5-dihydro-4,5-dioxo-1H-1-benzopyrano[2,3-b]pyridine-3-carboxylic acid.

7. A pharmaceutical composition for alleviating allergic manifestations in mammals comprising an effective amount of a compound of the formula VII.

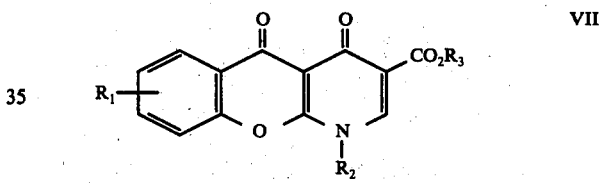

wherein $R_1$ is hydrogen, lower alkyl, hydroxy or lower alkoxy; $R_2$ is hydrogen or lower alkyl; $R_3$ is hydrogen or lower alkyl; and the pharmaceutically acceptable, non-toxic salts thereof, together with an inert pharmaceutical carrier therefor.

8. A method of preventing allergic manifestations in mammals in need thereof which comprises the administration of an effective amount of a compound of the formula VII:

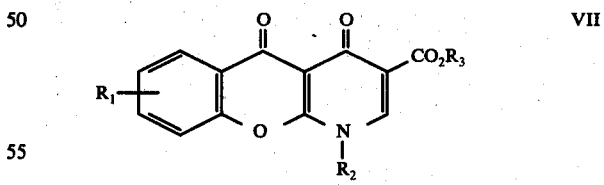

wherein $R_1$ is hydrogen, lower alkyl, halogen, hydroxy or lower alkoxy; $R_2$ is hydrogen or lower alkyl; $R_3$ is hydrogen or lower alkyl; and the pharmaceutically acceptable, non-toxic salts thereof.

* * * * *